US005738860A

United States Patent [19]
Schønfeldt et al.

[11] Patent Number: 5,738,860
[45] Date of Patent: Apr. 14, 1998

[54] NON-FIBROUS POROUS MATERIAL, WOUND DRESSING AND METHOD OF MAKING THE MATERIAL

[75] Inventors: Lars Schønfeldt, Snekkersten; Peter Sylvest Nielsen, Væløse; Peter Boman Samuelsen, Rungsted Kyst, all of Denmark

[73] Assignee: Coloplast A/S, Humlebaek, Denmark

[21] Appl. No.: 596,322

[22] PCT Filed: Aug. 19, 1994

[86] PCT No.: PCT/DK94/00312

§ 371 Date: Mar. 29, 1996

§ 102(e) Date: Mar. 29, 1996

[87] PCT Pub. No.: WO95/05204

PCT Pub. Date: Feb. 23, 1995

[30] Foreign Application Priority Data

Aug. 19, 1993 [DK] Denmark ............................. 0946/93

[51] Int. Cl.⁶ .......................... A01N 25/34; A61L 15/16
[52] U.S. Cl. .......................... 424/402; 424/404; 424/444; 424/445

[58] Field of Search ..................... 424/402, 404, 424/444, 445; 422/56, 60; 602/42, 43, 46

[56] References Cited

U.S. PATENT DOCUMENTS

| | | | |
|---|---|---|---|
| 4,906,488 | 3/1990 | Pera | 426/573 |
| 4,950,454 | 8/1990 | Masuda et al. | 422/56 |
| 5,149,469 | 9/1992 | Komatsuzaki et al. | 264/28 |
| 5,547,848 | 8/1996 | Shinoki et al. | 435/7.9 |

*Primary Examiner*—Thurman K. Page
*Assistant Examiner*—Kathryne E. Shelborne
*Attorney, Agent, or Firm*—Ostrolenk, Faber, Gerb & Soffen, LLP

[57] ABSTRACT

The invention concerns a porous material essentially consisting of one or more hydrophilic polymers and/or pharmaceutical water-soluble medicaments as well as optionally reinforcing elements and/or additives. The material has a structure essentially in the form of elongate leaf-like formations, which essentially extend in the same vertical direction, and which are united in longitudinal areas to provide vertically elongate pores located therebetween. The invention additionally concerns a wound dressing comprising such a material, and a method of making the material.

26 Claims, 3 Drawing Sheets

NON-FIBROUS POROUS MATERIAL, WOUND DRESSING AND METHOD OF MAKING THE MATERIAL

BACKGROUND OF THE INVENTION

This application is a 302SC371 of PCT DK 94/00312 filed Aug. 19, 1994.

The present invention concerns a non-fibrous porous material essentially consisting of one or more hydrophilic polymers and/or pharmaceutical water-soluble medicaments, a method of making such a material, and a wound dressing comprising such a material.

A large number of porous materials of the above-mentioned type are known today. Such materials find widespread use in the sick-care technology and are used e.g. in products for surgical or dental application, in haemophase-active products and implants. Such materials are moreover extensively used for the treatment of wounds.

Known products for haemophase include e.g. Suricet (Johnson & Johnson) based on oxidized regenerated cellulose, Collastat (Kendall) based on collagen, Thrombostat (Warner Lambert) based on prothrombin, and Spongostan (Ferrosan) based on gelatine.

Known products for wound treatment include in particular Sorbsan (Steriseal) based on calcium alginate, and Kaltostar (Brit Cair) based on sodium and calcium alginate.

In products of the type mentioned above, the structure of the material is of very great importance. Particularly, it has been found that the structure of the material is of great importance for its ability to rehydrate or absorb liquid, such as wound exudate and other exuding body fluids.

The object of the present invention is to provide a novel material of the type stated in the opening paragraph which has particularly good rehydration and/or absorption properties, and which therefore lends itself extremely well for use in or as wound treatment products, such as dressings.

As mentioned above, it is generally known to use porous hydrophilic polymer materials in wound dressings.

A wound dressing comprising such a porous hydrophilic polymer material is mentioned e.g. in SE published application No. 453 566. The dressing described in this document consists of an adhesive liquid permeable layer, a layer of a liquid impermeable film, and a layer of a porous hydrophilic polymer material with open pores interposed between said two layers.

DK patent application No. 1487/90 moreover describes a porous material for use in the treatment of wounds. The material is prepared by freeze-drying of a gel consisting of a hydrocolloid and a wound-healing component, such as growth hormone, to provide a porous material having evenly distributed pores.

Porous hydrophilic polymer materials based on polysaccharides rides are generally used in wound dressings because of their good properties with respect to giving the wound optimum healing conditions. The surrounding environment of the wound-is thus of great importance to the healing rate.

One of the most important properties of polysaccharide-based materials is their liquid absorbing ability. Thus, such materials are frequently used in occlusive and semipermeable dressings, since they absorb the wound exudate without desiccating the wound. It is important that the wound, and in particular the skin surrounding the wound, is not too wet, since the skin will then macerate and involve the risk of liquid running under the dressing, which may establish a passage for dirt and bacteria into the wound.

The known polysaccharide-based materials are most frequently in the form of fibrous woven or non-woven materials. Such materials are mentioned e.g. in the WO patent applications Nos. 80/02300 and 89/12471, U.S. Pat. No. 3,824,997 and EP patent application No. 476 756. The materials disclosed in these are mainly based on a mixture of alginate salts. However, such fibres greatly tend to stick to the rim of the wound or to leave residues in the wound when removed due to their poor integrity, which is very inexpedient, because the fragile newly formed tissue is easily damaged. It moreover involves the risk of the fibres sticking to the newly formed wound tissue.

The patent literature also includes some non-fibrous polysaccharide-based porous materials, e.g. in the form of foamed gels which are formed in situ at the wound site, a water-soluble alginate salt, a metal salt, an acid and a foam forming agent being mixed immediately before use. As will appear, this gel is very difficult and time-consuming to use and has a low absorption. Such a material is mentioned in EP patent application No. 380 253.

A similar material is disclosed in EP patent application No. 153 836. The material described in said application is present in a dry mixture, e.g. in tablet form, which forms a foamed gel when dissolved in water.

SU certificate No. 1 171 476 discloses a porous calcium alginate material which is made by freeze-drying of a solution consisting of calcium gluconate and sodium alginate. It is stated in the certificate that the product has a good integrity and lends itself for use as a wound dressing. However, it has never been used in practice, as far as is known.

JP patent applications Nos. 87-159494 and 87-166603 respectively disclose a collagen foam material and a method of making it. An essential aspect of the described collagen foam is that it contains at least 0.1% of a surfactant based on the dry weight of collagen. Such surfactants are not particularly expedient in foam materials which are to be applied to open wounds, in implants or the like.

Several of the known materials described above have a reasonable water absorbing capacity and moreover have a reasonable absorption rate and initial absorption ability. When applying a dressing to a very exuding wound, it is very essential that the material in contact with the wound is capable of absorbing or discharging the exudate just as rapidly as it is formed, since, otherwise, the dressing will create a poor wound healing environment and will perhaps result in liquid underflow and/or cause maceration of the surrounding skin.

It is moreover essential that the materials in contact with the wound have a high integrity even in a wetted state, so that they can be removed without leaving debris in the wound.

U.S. Pat. No. 5,149,469 describes a method of making a material which essentially has the properties described above. The material is made by freeze-drying of a gel of e.g. polyamino acid with a solvent, such as e.g. cyclohexane. The resulting material has an even distribution of pores, and the pore size may optionally be smaller in the surfaces of the material. The three-dimensional network of the material has a structure in the form of film-like bonds forming the open pores. This means that liquid can freely pass into the porous structure, while the film-like bonds impart a high strength to the material.

DESCRIPTION OF THE INVENTION

Figure 1A:
FIG. 1A is an SCM picture of a fractured face of material.

The inventors of the present invention have now surprisingly found a new material which, in addition to the good properties described above, is capable of rehydrating and/or absorbing liquid in a controlled manner, so that the direction of liquid passage through the material is under control.

Thus, the material of the present invention has the additional advantage that the liquid can pass through the material essentially just in a predetermined direction.

The present invention provides a non-fibrous porous material of one or more hydrophilic polymers and/or pharmaceutical water-soluble medicaments as well as optionally reinforcing elements and/or additives, characterized in that the material has a structure essentially in the form of elongate leaf-like formations, which essentially extend in the same vertical direction, and which are united in longitudinal areas to provide vertically elongate open pores located therebetween, and that the pore size varies systematically so that the pore size decreases vertically down through the material.

The term vertical direction is taken to mean any direction chosen beforehand, the horizontal direction mentioned below being defined on the basis of the vertical direction.

The elongate pores, which are oriented vertically, thus permit liquid to pass vertically through the material, but essentially prevent transverse or horizontal spreading of liquid in the material.

However, in an outermost surface layer, viz. the surface layer closest to the freeze mould in the production, which is described later, some horizontal spreading of liquid may occur, since the material in this surface layer normally has a considerably larger number of smaller pores and thereby a greater capillary effect than the rest of the material. The outermost layer of material discussed here has a thickness of 5–200 μm, in particular 5–100 μm, most frequently 5–50 μm.

This property is of great importance when the material is used in a wound dressing, since the material, when arranged against an exuding wound with the cell openings facing the wound, direct the exudate vertically away from the wound essentially without horizontal spreading of liquid, so that the skin around the wound is kept dry, thereby minimizing the risk of maceration of the wound-surrounding skin.

The material of the invention is likewise suitable for use in a large number of other products in which the above-mentioned property is desirable. These include e.g. products for surgical or dental use, haemophase-active products, implants and skin/wound treating products.

It is a special advantage of the material that it does not necessarily contain surfactants, since such agents frequently have cytotoxic effects when the material is used in e.g. wound treatment products.

The material of the invention may be designed for the specific use, since the material may be varied with respect to the outer form (size and shape), pore size and variations of the pore size through the thickness of the material, pore number (density of the material) as well as with respect to the composition of hydrophilic polymers and/or pharmaceutical medicaments, reinforcing elements and other additives.

For use in or as wound dressings, the material of the invention is preferably shaped as a mat or pad having at least one substantially plane face extending in the entire area extent of the material and intended for facing a wound, the face of the material being transverse to the pore orientation.

The mat or the pad may have the same thickness in the entire extent of the mat or the pad, or the thickness may vary according to the intended use of the material.

The pore size Of the material may be substantially uniform or vary arbitrarily or systematically. The cells of the material are preferably to have an average horizontal cross-sectional diameter of between 20 μm and 300 μm, preferably between 20 μm and 100 μm, and an average vertical length of more than 500 μm. The material in the form of a mat or a pad may advantageously have systematically varying pore sizes which vary vertically through the thickness of the material, so that they decrease in size at an increasing distance to the plane face which is intended to face the wound or the face from which liquid is to be absorbed. The average density of the material is preferably less than 100 $mg/cm^3$ and in particular between 15 and 35 $mg/cm^3$. The opposite face of the material, i.e. the one intended to face away from the face from which liquid is to be absorbed, may advantageously have very small pores and optionally be completely cross-linked to provide a liquid barrier.

In a particularly preferred embodiment of the invention, one, two- or three-dimensional networks are incorporated in the material. Such networks serve to increase the tear strength of the material and consist e.g. of woven, non-woven, plaited or moulded polymers, such as polystyrene, polyethylene, nylon, propylene, polyurethane or mixtures thereof. The network or networks preferably have a gram weight of between 2 and 15 $g/m^2$ as well as a mesh size of between 10 and 200 mesh. It is particularly preferred to arrange one or more sheet-shaped networks having a mesh size in the form of equilateral triangles with a lateral length of about 1 mm transversely to the orientation of the pores and extending in the entire area extent of the material. The optimum number of networks depends upon the thickness of the material, but usually a single network will be sufficient.

As mentioned, the material of the invention may comprise one or more hydrophilic polymers. Of course, these are selected according to the desired use of the material. Preferred hydrophilic polymers include in particular the following ones:

Synthetic: Polyvinyl pyrrolidone (PVD) and polyvinyl alcohol (PVAL), polyacrylic acids, polyacrylamide, polyethylene oxides, polypropylene oxides, copolymers of polymethyl vinyl ether and maleic acid anhydride.

Polysaccharides: Alginate, chitine, chitosan, pectin, carrageenan and various cellulose and starch compounds.

Biological: Gelatines, collagens and glycosamine glycanes (GAG's).

For dressings, it is particularly preferred to use one or more polysaccharides.

The polysaccharide material may comprise salts of one or more polysaccharides, preferably selected from alginate, pectin, pectate, gellan and carrageenan as well as one or more cations, preferably two or more cations, preferably $Na^+$, $K^+$, di- or trivalent cations, in particularly preferred being $Na^+$, $Ca^{2+}$, $Al^{3+}$, $Mg^{2+}$, $K^+$, $Z^{++}$ and chitosan.

Further, cations may advantageously be selected so that a first cation forms a water-soluble salt with the present polysaccharides, and a second cation forms a non-water-soluble or sparingly water-soluble salt with the present polysaccharides.

In a particularly preferred embodiment of the invention, the material consists of a mixture of Na and Ca alginate, preferably in the ratio 70:30–0:100.

The material of the present invention may moreover essentially be based on pharmaceutical medicaments or on a mixture of the above-mentioned hydrophilic polymers and pharmaceutical medicaments. Suitable pharmaceutical medicaments include e.g. growth hormones, polypeptide growth factors (TFG, FGF, PDGF, EGF) and others.

Further, the material of the invention may contain minor mounts of other medicaments, such as bacteriostatic or bacteridal compounds, e.g. iodine, iodine povidone complexes, chloroamine, chorohexidine, silver salts, metronidazole, sulpha compounds and penicillins, tissue healing promoting substances, e.g. RGD tripeptides and the like, enzymes for cleaning wounds, e.g. pepsin, trypsin, etc., cytotoxic agents and proliferation inhibitors for use when operating the product into cancer tissue, as well as other therapeutic agents which may optionally be applied topically.

The hydrophilic polymers may optionally be completely or partly cross-linked, e.g. via ion bonds. The higher the degree of cross-linking is, the less water-soluble the material is. This effect may therefore be utilized particularly in those cases where the material of the invention comprises both hydrophilic polymers and medicaments.

The material may additionally comprise minor amounts of various additives, including pH-adjusting additives, such as phosphate buffer, plasticizing additives, such as polyethylene glycols, deodorizing agents, such as chlorofylium and active carbon. If the additives have substantial surface-active properties, these are preferably present in amounts smaller than 0.1% based on the dry weight of hydrophilic polymers.

Thus, the wound dressing of the invention may consist of the material exclusively in the form of a mat or pad, which may advantageously be coated with the water-insoluble, liquid tight film or foam on the face intended to face away from the wound face.

In another preferred embodiment of the wound dressing, said dressing comprises an adhesive skin sheet, e.g. a hydrocolloid skin sheet on whose adhesive face a mat or a pad of the material is provided or depressed, so that the adhesive skin sheet extends beyond the mat along all the edges of the mat or the pad and thus form an adhesive frame around the mat or the pad.

A suitable hydrocolloid skin sheet is described e.g. in DK patent specifications No. 147 034 and No. 147 035 (corresponding to the U.S. Pat. No. 4,231,369 and No. 4,367,632).

The wound dressing of the present invention may moreover comprise skin sheet products containing other elastomers, e.g. as disclosed in U.S. Pat. No. 3,339,546.

The wound dressing of the invention may moreover comprise non-liquid absorbing skin sheet products, such as those known form WO patent application No. 90/01911, GB patent specification No. 128 631 and DK published application No. 158 493. Particularly useful are thin, non-liquid absorbing products. These include e.g. the skin sheet product Tegaderm® marketed by 3M, the skin sheet product Bioclosure® marketed by Johnson & Johnson, the skin sheet product OpSite® marketed by Smith & Nephew, and the skin sheet product Uniflex® marketed by Howmedica.

The thin non-absorbing products are extremely flexible and frequently transparent. They consist of a non-absorbing adhesive, such as rubber, various acrylates or copolymerisates thereof, polyvinyl ether and synthetic or natural resins and a film cover layer which is frequently waterproof, but has a relatively great water vapour permeability.

The skin sheet products described above are incorporated in the wound dressing of the invention e.g. by arranging a mat or a pad of the material of the invention centrally on the adhesive face of the skin sheet products, as described before. Further, skin sheet products of the invention may advantageously be constructed like the skin sheet products described in DK patent application No. 48/92 which include a porous material (particular reference to the embodiments shown in FIGS. 4 and 5). Other preferred wound dressings comprising the skin sheet products described above will be described later with reference to the drawings.

The present invention moreover concerns a method of making the material.

The method of the invention comprises the following steps:

a) dissolving one or more pharmaceutical medicaments and/or hydrophilic polymers in water to provide a solution or sol, b) prenucleating a freeze sheet by passive condensation or by evaporating or atomizing water or an aqueous solution of the pharmaceutical medicaments and/or hydrophilic polymers mentioned in a) and/or salts, e.g. salts containing cations which cross-link the hydrophilic polymers on a freeze sheet having a temperature which is lower than the freezing point of the water or the solution, c) applying the solution formed in a) to the prenucleated freeze sheet, whose temperature is to be kept constantly below the freezing point of the atomized water or solution, d) freezing the solution formed in a) to provide an ice sheet comprising the prenucleated frozen material, e) freeze-drying the ice sheet, and optionally f) cutting it in suitable sizes.

The pharmaceutical medicaments and/or hydrophilic polymers used in a) are fully or partly water-soluble. Particularly suitable pharmaceutical medicaments and/or hydrophilic polymers include the components mentioned in connection with the material of the invention. However, the solution may contain minor amounts of gellable polysaccharide salts, such as Ca alginate. It is preferred in particular that the solution has a viscosity of up to 800,000 cP, preferably up to 60,000 cP measured at 25° C. The solution may additionally contain water soluble or dispersible additives, foaming agents or other biological, active medicaments.

The solid content of the solution is of importance to the pore amount and the size of the finished material. This importance is described more fully below. It is particularly preferred that the solid content of the solution is 0.5 to 3.5% by weight.

As mentioned before, the material usually has more and smaller pores and thus a higher capillary effect in the area closest to the freeze sheet. If the material is to be used as a wound pad or dressing, the area of the highest capillary effect is placed most remotely from the wound so that the liquid from the wound flows vertically out into the pad or the dressing and then spreads horizontally in the layer having the highest capillary effect.

The pharmaceutical medicaments and/or hydrophilic polymers and optional additives may be stirred or whipped in the water in a simple manner. When the components have been mixed, the solution or the sol may advantageously be left to stand in order to achieve a maximum degree of dissolution and optional gelling, and air bubbles, if any, may simultaneously be expelled, if desired. However, in certain cases it may be desirable that the solution or the sol contains evenly distributed air bubbles, preferably air bubbles having an average size of below 100 μm, and in particular below 10 μm and a total volume of below 25%, preferably below 5% of the volume of the solution or the sol. To further the formation of air bubbles, a foam forming agent may optionally be added, such as mono/diglycerides and derivatives thereof (Amidan/Dimodam), Tweens, fatty acid salts (Na stearate), pluronic (polyethylene oxide/propylene oxide), lechitin, betaines, alkyl sulphates (sodium dodecyl sulphate SDS). The dissolution of the components may optionally be accelerated by heating, cooling or addition of acid/base or other dissolution-accelerating agents.

The freeze sheet mentioned in b) is preferably of a heat-conducting material, e.g. metal, and has a smooth surface, which is preferably plane. The freeze sheet is prenucleated with water or an aqueous solution of one or more pharmaceutical medicaments and/or water soluble or dispersible hydrophilic polymers or additives, such as salts containing cations, such as $Ca^{2+}$, $K^+$ and chitin/chitosan. The aqueous solution may e.g. be the solution prepared in a). The freeze sheet is cooled to a temperature which is lower than the freezing point of the prenucleation material and preferably to a temperature which is considerably lower than this freezing point. Optimally, the freeze sheet is cooled to between the freezing point and $-80°$ C., and in particular to between $-20°$ and $-60°$ C. The prenucleation material is atomized or evaporated in a thin layer on the freeze sheet, so that it immediately freezes, or the freeze sheet is left for passive condensation, which means that the moisture of the air is nucleated on the sheet. The latter, however, may be very time-consuming and difficult to control, for which reason active atomization or evaporation is preferred. The atomized liquid is preferably to have a drop size below 1,000 μm. The drop size determines the surface structure of the material, but has no significant influence on the microstructure. The average thickness of the atomization layer is preferably between 10 and 1,000 μm. However, the atomization layer must be so thick that it does not melt completely in the subsequent application of the medicament/polymer solution. Thus, the optimum thickness of the atomized layer depends on the temperature parameters of the process.

After the prenucleation of the freeze sheet, the medicament/polymer solution is placed on the sheet, optionally by applying it as a plane layer, said freeze sheet being kept below the freezing point of the prenucleation material and preferably far below it so as to avoid complete melting of the frozen prenucleation layer.

The medicament/polymer solution may optionally be applied in several layers, it being possible to arrange between the layers a sheet-shaped or three-dimensional network which is hereby embedded in the material. Alternatively, a network may be put on the placed/applied medicament/polymer solution and be pushed gently down into the solution. Various configurations of networks can be obtained hereby. Suitable networks have been mentioned before in the description of the product.

The medicament/polymer solution is then frozen by discharging heat. Freezing preferably takes place by discharging heat from the face directed toward the freeze sheet and optionally from the face directed away from the freeze sheet. The rate of freezing influences the pore size of the finished material. The faster the freezing, the smaller the pores. Thus, the pore size can be varied as desired through the material by freezing from various directions. Optimally, the rate of freezing is between 0.05 and 3 mm/min.

The frozen ice sheet comprising the frozen solution and the frozen prenucleation layers is then freeze-dried. Before freeze-drying, the ice sheet may optionally be transferred to a perforated plate or other suitable freeze-drying substrate. To avoid curving or bending of the material, the ice sheet may e.g. be retained between two plates during the freeze-drying process. The freeze-drying then proceeds in a generally known manner and e.g. as described in the examples below.

In an alternative embodiment, the material of the invention is prepared in several layers by prenucleating the freeze sheet, applying a first layer which is then frozen, prenucleating again on top of the first frozen layer e.g. by $H_2O$ spraying and then applying another layer on top of the first one. During freeze-drying, the two xerogels are separated by sublimation of the intermediate prenucleation layer. The same morphology is obtained on the two sheets. The process may be extended to moulding of ice blocks consisting of many sheets.

After completed drying, i.e. between steps e) and f), the material, if polysaccharides are included, may be converted by ion exchange or application of ions, thereby simultaneously forming cross-links between the polysaccharides, which stabilizes the material and reduces its water solubility.

The ion exchange or application takes place by treating the material with a cation-containing solution. The solvent consists of a mixture of water and one or more other fluid components, said water constituting between 0 and 95% by weight of the solvent. If the solvent contains less than 10% water, ion application is preferably employed, whereas a higher water content results in ion exchange proper. The other fluid component or components are selected such that they essentially do not act as a structure-destroying solvent for the material which is to be converted, and which, however, is capable of maintaining a reasonable cation strength, i.e. a cation strength corresponding to minimum 0.01 mol cation/l solution. The cation or ions are preferably capable of forming water-insoluble salts with the polysaccharides present in the material. Particularly suitable cations include $K^+$, di- and polyvalent cations, in particular $Ca^{2+}$, $Zn^{2+}$, $Al^{3+}$, $Mg^{3+}$, $K^+$, chitin and chitosan. The anion is selected so that it is essentially inert to the material to be converted. Suitable cations include e.g. $Cl^-$, $Br^-$, $I^-$, $CO_3^{2-}$, $SO_4^{2-}$, acetate and lactate. The concentration of ions in the solution is preferably to be between 10 and 100% of the degree of saturation.

The ion exchange or application may proceed in one or more steps by dosing the cation solution on one face of the material and sucking it through the material, and repeating this a suitable number of times, the material being optionally flushed with an ion-free or ion-poor liquid solvent after each step.

The degree of conversion achieved depends on the number of treatment steps, the amount of solvent per unit of material, the wetting time, the ion concentration in the solvent and the composition and temperature of the solvent.

The ion exchange/application process may advantageously be performed as a continuous band filtration process. Following completed ion exchange/application, the material may optionally be re-dried, if necessary.

As appears from the above, pore sizes and number of pores in the finished material mainly depend on two parameters, viz.

a) concentrations of hydrophilic polymers or medicaments in the solution which is frozen, and b) freezing rates.

Parameter a) is of importance to the density of the prepared material. The higher the concentration, the higher the density.

Parameter b) is of importance to the pore size. The faster the freezing, the smaller the pores.

Parameter a) is the same for the material through its entire thickness and width, whereas parameter b) may be varied e.g. by freezing from several sides at different freezing rates.

The drop size of the atomized prenucleation liquid and the composition of the liquid (parameter c)) are of importance to the surface morphology of the face closest to the freeze sheet. The roughness/smoothness of the surface may be adjusted as desired by adjusting parameter c).

It is thus possible to design a material having a surface morphology, pore size, pore number and pore distribution as desired by varying the parameters a), b) and c).

The invention will be described more fully below and with reference to examples and drawings.

EXAMPLE 1

A base solution is prepared by dissolving 100 g of Sorbalg PH125 sodium alginate (Grindsted Products, Denmark) in 3900 g of distilled $H_2O$ with planet mixer Bjørn R10 (A/S Wodschow & Co., Denmark). The viscosity is about 10,000 cP at 20° C.

The solution is frozen to an about 4 mm thick ice sheet with one-sided heat discharge from a horizontal liquid-cooled steel freeze plate (Heto/Holten). The temperature of the freeze plate is maintained at about −20° C., which involves a vertical temperature gradient of about 40° C. to the surrounding room temperature of about 20° C.

Horizontal crystal growth during freezing is prevented by prenucleating with distilled $H_2O$ on the freeze plate prior to application of the alginate solution. This results in a uniform heterogeneous nucleation base for vertical crystal growth in the alginate solution.

The prenucleation involves directing vapour across the freeze plate (−20° C.) for about 20 sec., until the freeze plate has been coated with about 400 µm thick ice (white frost).

The alginate solution is moulded on the white frost layer on the freeze plate in the following manner. The solution is poured onto the plate and distributed with a metal rail/scraper which is pressed against two parallel 4 mm thick metal guide rails mounted on the freeze plate so that the layer of alginate solution has a thickness of about 4 mm. The freezing time is about 15 min.

The freeze-drying is performed in CD8 (Heto/Holten, Denmark) at 1 hPa and max. shelf temperature of 30° C.

EXAMPLE 2

A material is prepared as stated in example 1, the freeze plate being prenucleated by spraying with distilled $H_2O$ drop diameter 10–200 µm in a layer of about 500 µm.

EXAMPLE 3

A material is prepared as stated in example 2, there being used a 1 weight percent aqueous sodium alginate solution for the prenucleation, the temperature of the freeze plate being maintained at about −40° C., which involves a temperature gradient of about 60° C. to the surrounding room temperature of about 20° C.

EXAMPLE 4

A material is prepared as stated in example 2, there being used a 1 weight percent aqueous $CaCl_2$ solution for the prenucleation.

EXAMPLE 5

A material is prepared as stated in example 2, there being used a 1 weight percent aqueous chitosan solution for the prenucleation.

EXAMPLE 6

A material is prepared as stated in example 1, the base solution being made of about 150 g of Protanal LF10/60 RB (Pronova Biopolymers, N), dissolved in about 4850 g of distilled $H_2O$.

EXAMPLE 7

A material is prepared as stated in example 1, the base solution having been replaced by Na/Ca alginate gel, which consists of 80 g of Protanal LF120M sodium alginate (Pronova Biopolymers, N)+320 g of Protanal TXF 200 calcium alginate (Pronova Biopolymers, N) dissolved in 3600 g of distilled $H_2O$. Further, 40 g of GDL (Glycoldelta lactol) (Sigma G4750) are added. Freezing is performed within 2 hours of mixing.

EXAMPLE 8

The material prepared as stated in example 1 (called xerogel below) was converted by two different recipes using the following process.

A sodium alginate xerogel as described in example 1 is punched 6×6 cm. The xerogel is placed in a Petri dish, and 15 ml of reagent (see the scheme) are added. The Petri dish is provided with a lid, followed by sealing with faucet grease. After standing for about 30 sec. at 20° C., approximately 80% by weight of the sucked reagent is filtered on a Büchner funnel by water jet pump. A frit glass filter having a 40–100 µm pore diameter is used. Then the moist xerogel is washed twice with 15 ml of washing solvent (see the scheme), which is distributed evenly over the xerogel placed on the Büchner funnel. Vacuum is disconnected during the addition of the solvent, and immediately afterwards about 80% by weight of the solvent is sucked off, and the washing procedure is repeated.

Following the last wash, the xerogel is dried at 40° C. for 4 hours between plane-stretched polyester nets.

| | Recipe I | |
|---|---|---|
| | Reagent | Washing solvent |
| 96% ethanol (D.D.S.F.) | 729.2 g | 937.5 g |
| Distilled $H_2O$ | 25.1 g | 53.5 g |
| $CaCl_2$ anhydr. (Sigma) | 20.0 g | 10.0 g |

| | Recipe II | |
|---|---|---|
| | Reagent | Washing solvent |
| 99.9% ethanol (D.D.S.F.) | 950.0 g | 950.0 g |
| Distilled $H_2O$ | 20.0 g | 20.0 g |
| $CaCl_2$ anhydr. (Sigma) | 30.0 g | 30.0 g |
| Glycerol (Sigma) | | 20.0 g |

EXAMPLE 9

Sodium alginate xerogel is prepared as mentioned in example 1, but with the modification that the freezing of the alginate solution takes place in three steps.

After prenucleation, the freeze plate is coated with 2 mm alginate solution according to the method described in example 1. HDPE Net 909 SN11 (Smith & Nephew, England) is applied to the surface, and another 2 mm alginate solution is applied. Following freeze-drying, the net-reinforced xerogel is converted according to example 8, recipe I.

EXAMPLE 10

A 2.5% weight percent of sodium alginate solution like in example 1 is admixed with a 2% Dimodan PM (Grindsted Products) solution (see the foam recipe). The latter is "activated" in a laminar liquid crystalline phase. Foaming is performed with the equipment mentioned in example I until 80% relative density with maximum stirring rate. Foaming time 5–10 min. with a 60° C. sodium alginate solution and 30°–35° C. Dimodan solution at the beginning. The foam is frozen and freeze-dried according to example 1.

Activation of 2% Dimodan PM is performed at 65°–67° C. on a water bath. 490 g of distilled $H_2O$ in a beaker are admixed with 10 g of Dimodan PM and 0.2 ml of 1.0M NaOH. When the liquid is homogeneous, it is removed from the water bath and cooled voluntarily at room temperature to less than 35° C.

Foam Recipe:

| | |
|---|---|
| 2.5% sodium alginate PH125 (see example 1) | 3000 g |
| 2.0% activated Dimodan PM | 150 g |
| (10 g Dimodan PM | |
| 490 g distilled $H_2O$ | |
| 0.2 ml 1.0 NaOH) | |

EXAMPLE 11

The sodium alginate material prepared in example 10 is converted to Na/Ca alginate as stated in example 8, recipe I.

EXAMPLE 12

A suspension consisting of 25 g of Gantrez AN-119 (polymethyl ether maleic anhydride) (GAF), 50 g of glycerol and 25 g of distilled $H_2O$ is applied to a PE film in a thickness of 2 mm. A PE film is placed on top, and the two films are welded together to a closed square. The welded PE bag with the polymer suspension is immersed in a water bath 90° C. for 1.5 hours. Gantrez is hereby cross-linked with glycerol by esterification.

The PE films are removed from the gel and frozen like in example 1 by rolling onto the white frost layer on the freeze plate. Freeze-drying also like in example 1.

EXAMPLE 13

A 1.0% wt Blanose 9H4XF (Hercules) solution in distilled $H_2O$ is prepared, frozen and freeze-dried according to example 1.

The NA-CMC xerogel is cross-linked with $Al^{3+}$ after freeze-drying—method according to example 8. Reagent and washing solvent appear from recipe III.

| Recipe III | | |
|---|---|---|
| | Reagent | Washing solvent |
| 96% ethanol (D.D.S.F.) | 900.0 g | 1,000.0 g |
| Distilled $H_2O$ | 95.0 g | |
| $AlCl_3.6H_2O$ (Sigma) | 5.0 g | |

EXAMPLE 14

A further 10 g of Chondroitin sulphate AC 99% (Løvens Kemiske Fabrikker) is added to the base solution of example 1. Freezing and freeze-drying are performed like in example 1: the xerogel is converted according to example 8, recipe II.

CLINICAL/ANIMAL EXPERIMENT

EXAMPLE 15

An alginate dressing according to example 9 (CP alginate) was compared with Kaltostat (Brit Cair) on exuding venous leg sores. The study was performed on eight patients, divided into two groups of four patients each, i.e. each dressing was tested on four wounds. For both dressings, gauze was used as a secondary fixation dressing and a pressure dressing was subsequently applied. The observed parameters were as follows: dressing wear time, healing rate by weekly measurement of area, ability to remove the dressing in one piece, as well as debris of the dressing in wounds and wound edges.

| | CP alginate | Kaltostat |
|---|---|---|
| Wear time | 3.5 ± 0.6 days | 2.2 ± 0.8 days |
| Healing rate per week | 4.1 ± 2.1% | 3.9 ± 2.3% |
| Ability to be removed in one piece | very good | good |
| Debris of the dressings in wounds and wound edges | none | many |
| Side effects | none | Maceration of the skin around the wound |

CP alginate thus gives a longer period of use, no debris in wounds and wound edges and no side effects in the Use of the dressing.

EXAMPLE 16

The alginate material of the invention (example 9) was compared with Sorbsan (Steriseal) by studying wound healing in pigs. The dressings were studied on 12 full thickness wounds, divided into two groups, i.e. six wounds were treated with CP alginate, and six wounds were treated with Sorbsan. A non-absorbing dressing (Tegaderm, 3M) was used as a secondary dressing.

The dressings were changed day 1, day 2, day 4, day 7 and day 10 in order to observe the ability of the dressings to absorb liquid and the integrity of the dressings.

The ability of the dressings to absorb exudate from the wounds on day 1, day 2 and day 4 was as follows:

|  | Absorption on day 1 | Absorption on day 2 | Absorption on day 4 |
| --- | --- | --- | --- |
| CP alginate | 0.29 ± 0.05 g/g | 0.28 ± 0.02 g/g | 0.31 ± 0.07 g/g |
| Sorbsan | 0.15 ± 0.04 g/g | 0.14 ± 0.03 g/g | 0.16 ± 0.05 g/g |

There is thus a significant difference between the abilities of the dressings to absorb liquid from the wounds.

When changing the dressings, the CP alginate could be removed from the wounds in one coherent piece on all the days. For all wounds treated with Sorbsan, dressing debris was found in the wound and in the wound edge.

The pigs were killed on day 14, and the wounds were studied histologically. Fibre debris were found in the granulation tissue for four wounds treated with Sorbsan. Macrophages were present around the fibres, apparently in the process of degredating the debris. No debris was found in the wounds for any of the wounds treated with CP alginate. All the wounds had healed on day 14.

Treatment of wounds with CP alginate thus results in a better wound tissue quality.

EXAMPLE 17

The material prepared in example 9 was tested for its ability to counteract horizontal spreading of liquid compared with the horizontal liquid spreading ability of commercially available alginate materials.

The test was performed in the following manner:

A wafer (∅=38 m, thickness 3.7 mm) of open-pored foam is saturated with 0.9% NaCl admixed with phenyl blue. The wafer is placed on a plane water-repelling plate. A 5×5 cm sample of dressing or material is placed centrally over the wafer with a plane bottom 250 g weight above. Both the weight and the sample are removed after 10 sec. The liquid spreading area is measured with cream image analysis equipment. The liquid spreading area in relation to the wafer area is an expression of the extent of horizontal swelling≧1.

A test was performed on Alginat Pad (according to example 9), Kaltostat® and Sorbsan®.

The relation between the results was as follows:

Kaltostat/Alginat Pad=2.2.

Sorbsan/Alginat Pad=2.4

Sorbsan/Kaltostat=1.1

It will be seen that Alginat Pad has a much smaller horizontal swelling than Sorbsan and Kaltostat, which have almost identical properties.

Figure 1B:
FIG. 1B is an SCM picture of a first face of material.
Figure 1C:
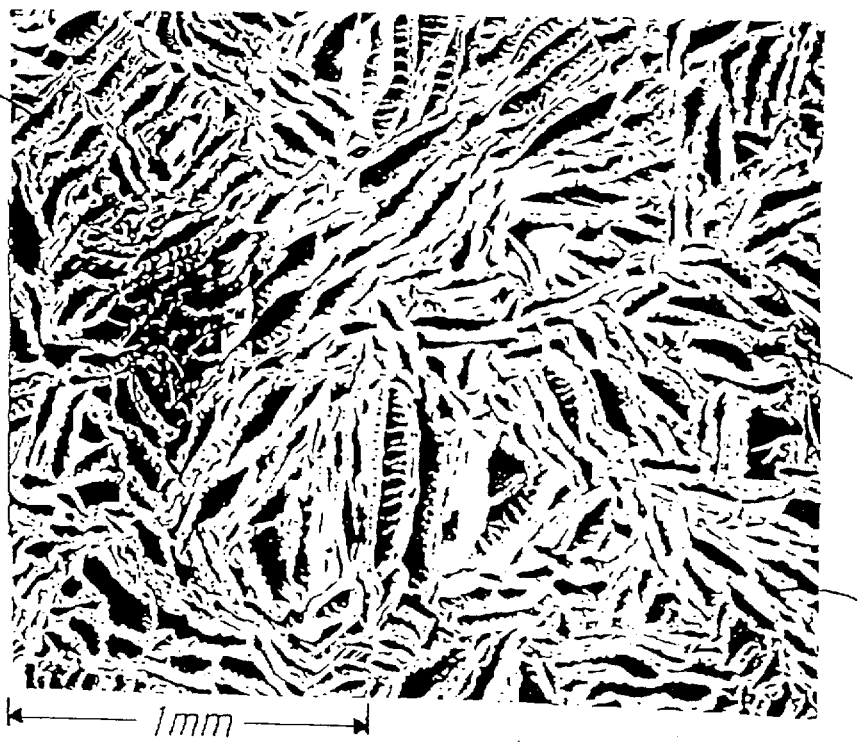
FIG. 1C is an SCM picture of a second face of material.

FIGS. 1A–1C show pictures of a material according to the invention, seen in section from the first face and from the second face, respectively.

FIGS. 2–7 are sectional view of various embodiments of dressings according to the invention.

FIGS. 1A–1C are SEM pictures of a material prepared as described in example 6. FIG. 1A shows a fractured face of the material. It will be seen that the pores 1 extend from the first face 2 toward the second opposite face (not shown). It will moreover be seen that the porosity of the material increases at an increasing distance from the first face. The pores are surrounded by elongate leaf-like formations 3. FIGS. 1B and 1C show SEM pictures of the first face and the second face, respectively. The first face was directed toward the freeze plate in the freeze-drying process, and it appears from FIG. 1B that there is an even distribution of open pores initiated from said first face. The second face has a large number of open pores. When using the material in a product, the material is preferably arranged so that the second face may be used as a contact face with the liquid to be absorbed by or to dissolve the material.

In the simplest embodiment, the wound dressing of the invention consists of the material of the invention just cut in suitable pieces, e.g. 9×9 cm and with a thickness of up to 1 cm, the thickness and the size depending on the composition of the material and the purpose of the dressing, of course. If the material is water-soluble, a dressing consisting of this material alone may advantageously be attached using a liquid-absorbing adhesive dressing, such as a dressing of the brand Comfeel® (Coloplast). The dressing shown in FIG. 2 consists of a first layer 10a of a material according to the invention, a second layer of a material 10b according to the invention as well as an embedded net 11. The two layers 10a and 10b are preferably of the same material and are united in the net spaces. The dressing may e.g. have been prepared as described in example 9. The dressing may be of any shape in terms of area, so that the area extent of the faces 12a and 12b may be square, rectangular, round, oval or the like, and also the size of the dressing may be chosen to suit the use. The dressing may optionally be prepared in rolls which can be cut as desired. Using the dressing shown in FIG. 2, the user can freely decide which face 12a or 12b is to be directed toward the wound. Frequently, however, the porosity will differ, and it is then preferred that the face of the greatest porosity is directed toward the wound.

Figure 2:
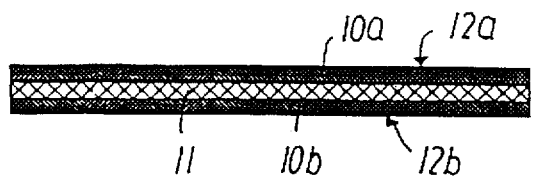
FIG. 2 shows a first embodiment of the invention.
Figure 3:
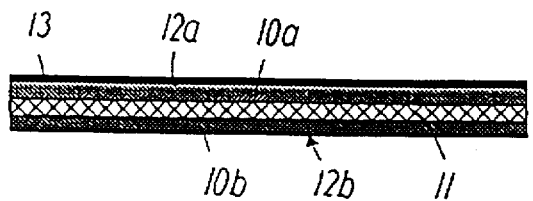
FIG. 3 shows a second embodiment of the invention.

FIG. 3 shows a variation of the dressing shown in FIG. 2, the layers 10a, 10b, 11 and the faces 12a and 12b referring to layers and faces which correspond to those shown in FIG. 2 with the same references. In the dressing shown in FIG. 3, the face 12b is intended to face a wound, said face 12a being covered by or coated with a flexible film layer 13, which is preferably liquid proof, such as polyurethane and other polymer films which are normally used as backings for wound dressings.

The dressings shown in FIGS. 2 and 3 are not adhesive or only so to a small degree, so in use they have to be fixed using a secondary dressing or film adhesive.

Figure 4:
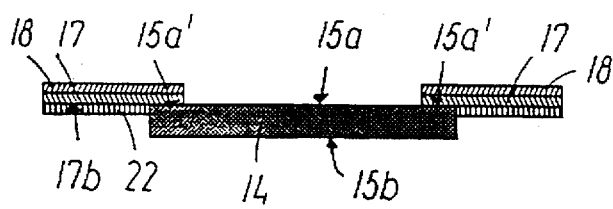
FIG. 4 shows a third embodiment of the invention.

The dressing shown in FIG. 4 consists of a layer 14 of a material according to the invention, optionally having embedded networks (not shown). The layer 14 has a first face 15a and a second face 15b which may be of any extent, i.e. the course of the periphery may be round, rectangular or the like. An adhesive layer 17 having a backing layer 18 is attached along the peripheral part 15a' of the first face 15a, said layers extending beyond the periphery of the layer 14 to provide an adhesive attachment frame by means of which the dressing can be secured to the user's skin. Prior to use, the adhesive face 17a of the adhesive layer on the part extending beyond the layer 14 has been covered by protecting, releasable silicone-coated paper 22 or the like.

Figure 5:
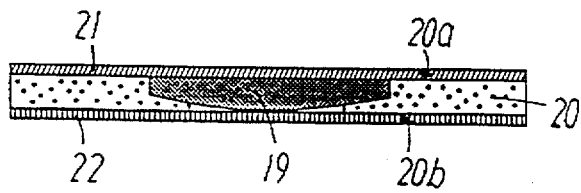
FIG. 5 shows a fourth embodiment of the invention.

The dressing shown in FIG. 5 consists of a layer 19 of a material according to the present invention embedded or impressed into a hydrocolloid-containing adhesive layer 20 and coated with a film backing layer 21, which likewise extends beyond the face 20a of the adhesive layer. The second face 20b of the adhesive layer is coated with a silicone-coated release layer 22 which is removed before use. The layer 19 is convex so that it is thinner in the peripheral part than in the central part, whereby the layer 19, in the shown embodiment, extends through the face 20b and will thus be in direct contact with the wound in use. In an alternative embodiment (not shown), the layer 19 has the same thickness in its entire area extent, and the entire face 20b is thus continuous.

Figure 6:
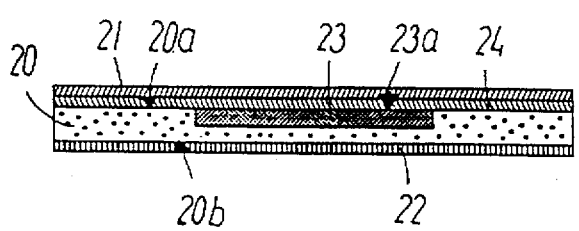
FIG. 6 shows a fifth embodiment of the invention.

FIG. 6 shows a dressing corresponding to the alternative dressing described above, the layers 20, 21, 22 and the faces 20a and 20b corresponding to layers and faces having the same references in FIG. 5, and the layer 23 has a uniform thickness in its entire area extent. The backing layer 21 and the adhesive face 20a respectively the face 23a have interposed between them a thin adhesive layer 24 of e.g. an acrylic adhesive for reinforced fixation of the layer 23 to the backing layer 21. This reinforced fixation is advantageous in particular in case of dressings to be used for highly exuding wounds.

Figure 7:
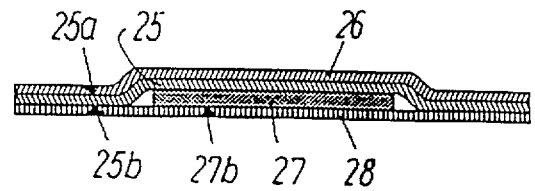
FIG. 7 shows a sixth embodiment of the invention.

The dressing shown in FIG. 7 is a so-called island dressing and consists of an adhesive layer 25 having a first side face 25a coated with a water impermeable film 26, and a second side face 25b on whose central part a layer 27 of a material according to the invention is attached. Before use, the free face 27b of the layer 27 and the second side face 25b of the adhesive layer on the part which is not coated with the layer 27, are coated with a removable release layer 28.

We claim:

1. A non-fibrous porous material consisting essentially of one or more hydrophilic polymers and/or pharmaceutical water-soluble medicaments as well as optionally reinforcing elements and additives, characterized in that the material has a structure essentially in the form of elongate leaf formations, which essentially extend in the same vertical direction, and which are united in longitudinal areas to provide vertically elongate open pores located therebetween, and that the pore size varies systematically so that the pore size decreases vertically down through the material.

2. A material according to claim 1, characterized in that the leaf formations essentially extend through the entire vertical thickness of the material.

3. A material according to claim 1, characterized in that there is less than 0.1% by weight of surfactant based on the dry weight of hydrophilic polymer.

4. A material according to claim 1, characterized in that the pores have an average transverse diameter of between 20 and 300 µm, and an average vertical length of more than 500 µm.

5. A material according to claim 1, comprising polysaccharide, and the material having a reinforced face with polymer.

6. A material according to claim 1, characterized in that it is shaped as a mat or pad.

7. A material according to claim 1, characterized in that it comprises salt of one or more polysaccharides selected from the group consisting of alginate, pectin, pectat, gellan and carrageenan, as well as one or more cations.

8. A material according to claim 1, characterized in that is consists essentially of Na and Ca alginate in a ratio 70:30–0:100.

9. A wound dressing, which comprises a material according to claim 1.

10. A wound dressing according to claim 9, characterized in that the material is in the form of a mat or pad, where the pores of the material are oriented transversely to the faces of the mat or pad, said pores having a minimum size adjacent a first face and a maximum size adjacent a second face.

11. A wound dressing according to claim 9, characterized in that it comprises an adhesive skin sheet and said material in the form of a mat or pad which is arranged on or inserted or impressed into the adhesive face of the skin sheet so that the skin sheet extends beyond the edges of the mat or pad.

12. A method of making a biocompatible, non-fibrous porous material, comprising the step of a) dissolving one or more pharmaceutical medicaments or hydrophilic polymers in water to provide a solution or sol, b) prenucleating a freeze plate by passive condensation or by evaporating or atomizing water or an aqueous solution of the pharmaceutical medicaments or hydrophilic polymers used in a) or salts, c) providing the solution formed in a) on the prenucleated freeze plate, whose temperature is kept constantly below the freezing point of the atomized water or the solution, d) freezing the solution formed in a) to provide an ice plate comprising the prenucleated frozen material, e) freeze-drying the ice plate, and optionally f) cutting it in suitable sizes.

13. A method according to claim 12, characterized in that the solution prepared in a) comprises a hydrophilic polymer selected from the group consisting of polyvinyl pyrrolidone, polyvinyl alcohol, gelatine, collagen, glycosamine glycane, polyacrylic acid, polyacrylamide, polyethylene oxide, polypropylene oxide, copolymer of polymethyl vinyl ether and maleic acid anhydride and polysaccharide.

14. A method according to claim 12, characterized in that the solution prepared in a) comprises pharmaceutical medicaments selected from the group consisting of growth hormones and polypeptide growth factors.

15. A method according to claim 12, characterized in that the solution has a total solids content of hydrophilic polymers and pharmaceutical medicaments of 0.0 to 3.5% by weight and a viscosity of up to 800,000 at 25° C.

16. A method according to claim 12, characterized in that the prenucleation liquid is atomized on the freeze plate with a drop size of below 1000 µm, and that the prenucleation layer has an average thickness of between 10 and 1000 µm.

17. A method according to claim 12, characterized in that the solution comprises one or more polysaccharides, and that the prenucleation liquid contains calcium ions for cross-linking and reinforcing the material.

18. A method according to claim 17, characterized in that the material is converted by ion exchange or ion application.

19. A non-fibrous porous material, characterized in that it is obtainable by the method of claim 12.

20. A method according to claim 13, characterized in that the solution prepared in a) comprises a polysaccharide selected from the group consisting of alginate, pectin, pectate, gellan and carrageenan.

21. A method according to claim 20, characterized in that the solution comprises a mixture of calcium/sodium alginate and the solution has a viscosity of up to 60,000 cP at 25° C.

22. A material according to claim 2, characterized in that there is an intermediate reinforcing layer interposed between the formations.

23. A material according to claim 4, characterized in that the pores have an average transverse diameter between 20 and 100 µm.

24. A material according to claim 6, characterized in that the mat or pad has at least one essentially plane face which extends transversely to the pore orientation, and which extends essentially in the entire area extend of the mat or pad.

25. A material according to claim 7, characterized by having at least two cations selected from the group consisting of sodium, potassium, calcium, aluminum, magnesium, zinc and chitosan.

26. A wound dressing according to claim 10, characterized in that said first face is coated with a water-insoluble liquid proof polymer film.

* * * * *